(12) United States Patent
Daffas

(10) Patent No.: US 12,070,327 B2
(45) Date of Patent: Aug. 27, 2024

(54) PAIN ASSESSMENT METHOD AND SYSTEM

(71) Applicant: Electronic Pain Assessment Technologies (EPAT) Pty Ltd, Subiaco (AU)

(72) Inventor: Philip Anastasis Daffas, Mosman (AU)

(73) Assignee: Electronic Pain Assessment Technologies (EPAT) Pty Ltd, Subiaco (AU)

( * ) Notice: Subject to any disclaimer, the term of this patent is extended or adjusted under 35 U.S.C. 154(b) by 382 days.

(21) Appl. No.: 17/553,451

(22) Filed: Dec. 16, 2021

(65) Prior Publication Data

US 2022/0104760 A1    Apr. 7, 2022

Related U.S. Application Data

(63) Continuation of application No. PCT/AU2020/050665, filed on Jun. 26, 2020.

(30) Foreign Application Priority Data

Jun. 28, 2019 (AU) .................................. 2019902296
Jul. 5, 2019 (AU) .................................. 2019902390

(51) Int. Cl.
*G16H 50/30* (2018.01)
*A61B 5/00* (2006.01)
*G06V 40/16* (2022.01)

(52) U.S. Cl.
CPC .......... *A61B 5/4824* (2013.01); *A61B 5/0004* (2013.01); *A61B 5/742* (2013.01); *A61B 5/746* (2013.01); *G06V 40/165* (2022.01); *G06V 40/167* (2022.01); *G06V 40/176* (2022.01); *G16H 50/30* (2018.01)

(58) Field of Classification Search
CPC ..... A61B 5/4824; A61B 5/0004; A61B 5/742; A61B 5/746; A61B 5/004; A61B 5/1128; A61B 5/0022; A61B 5/16; A61B 5/163; A61B 2576/02; A61B 5/72; G06V 40/165;
(Continued)

(56) References Cited

U.S. PATENT DOCUMENTS

2002/0030682 A1   3/2002   Eberlein
2009/0124863 A1   5/2009   Liu et al.
(Continued)

OTHER PUBLICATIONS

International Search Report and Written Opinion of the International Searching Authority mailed Aug. 28, 2020 in International Patent Application No. PCT/AU2020/050665. 11 pages.
(Continued)

*Primary Examiner* — Chuong A Ngo
(74) *Attorney, Agent, or Firm* — Kilpatrick Townsend & Stockton LLP

(57) ABSTRACT

A method for determining a representation for a level of pain experienced by a patient, the method comprising: providing reference information concerning at least two visible features that are indicative of experienced pain; capturing information indicative of facial features by observing the patient directly or indirectly over a predetermined time period; allocating at least one pain indicator corresponding to each feature based on the captured information; and collating each indicator to construct the pain level indicator.

19 Claims, 4 Drawing Sheets

(58) Field of Classification Search
CPC .. G06V 40/167; G06V 40/176; G06V 40/174; G16H 50/30; G16H 40/63; G16H 50/20
See application file for complete search history.

(56) References Cited

U.S. PATENT DOCUMENTS

| | | |
|---|---|---|
| 2013/0018275 A1 | 1/2013 | Dodson |
| 2014/0213845 A1 | 7/2014 | Bechtel et al. |
| 2017/0156661 A1 | 6/2017 | Hughes et al. |
| 2018/0193652 A1* | 7/2018 | Srivastava ............ A61N 1/0534 |
| 2019/0298253 A1* | 10/2019 | Hal ....................... A61B 5/6804 |
| 2019/0341147 A1* | 11/2019 | Lord ...................... G16H 40/20 |

OTHER PUBLICATIONS

International Preliminary Report on Patentability mailed May 17, 2021 in International Patent Application No. PCT/AU2020/050665. 70 pages.

\* cited by examiner

PAIN ASSESSMENT METHOD AND SYSTEM

CROSS-REFERENCES TO RELATED APPLICATIONS

This application is a continuation application of International Patent Application No. PCT/AU2020/050665 entitled "PAIN ASSESSMENT METHOD AND SYSTEM," filed on Jun. 26, 2020, which claims priority to Australian Patent Application No. 2019902390, filed on Jul. 5, 2019, and Australian Patent Application No. 2019902296, filed on Jun. 28, 2019, each of which are herein incorporated by reference in their entirety for all purposes.

TECHNICAL FIELD

The present disclosure relates to a pain assessment system and a method for determining a representation of the amount of pain experienced by a patient.

BACKGROUND

Pain assessment amongst non-communicative patients such as patients with dementia or infants is difficult and highly subjective. Patients with dementia commonly have pain, and this pain often goes undetected and under treated. Undiagnosed pain can manifest in other symptoms such as increased confusion and behavioural change such as agitation and aggression which may lead to difficulties with delivering care, increased medication use and carer burden.

Existing tools that are based on American Geriatric Society's (AGS) guidelines are not automated, highly subjective resulting in significant variability, and hence inconsistencies in pain management of patients.

There is need for improvement.

BRIEF SUMMARY

In accordance with a first embodiment, there is provided a method for determining a representation of pain experienced by a patient, the method comprising:
 capturing information concerning at least two visible features or sets of features that are indicative of experienced pain by observing the patient directly or indirectly over a predetermined time period;
 allocating at least one pain indicator to each feature or set of features based on the captured information, each pain indicator comprising a distinct visual component; and
 collating all pain indicators to construct the pain representation,
 wherein the pain indicator is allocated in dependence on a determined pain severity, and
 wherein the pain representation comprises a display of at least two pain indicators so that their corresponding visual components are simultaneously visible.

The visible facial features or set or features may correspond to facial expressions analysed using the FACS (Facial Action Coding System) methodology. The sets of features may correspond to action units. Each pain indicator may correspond to one or more action units.

The allocation of the pain indicator may be made with reference to reference information. In an embodiment, computer software has been pre-trained to determine which action units correspond to pain. In such an embodiment, the computer system will refer to the reference information generated during training to determine whether or not a particular facial feature or set of facial features corresponds to pain. In addition, or alternatively, reference information pertaining to a patient who is experiencing no, or less, pain may be used the allocation is then made on the basis of a determined increase in pain.

Human observers suffer from a lack of objectivity, resulting in a lack of consistency between observers and patients. However, the ultimate decision regarding how to treat pain still resides with the human medical practitioner. Therefore, embodiments may provide more consistent and reliable pain representations than a human observer working on their own, further helping to ensure timely intervention for those patients suffering from pain. By representing visual components of the pain indicators simultaneously, embodiments may allow a more objective evaluation of the pain representation. This may be particularly true where the indicators are displayed with historical information so that the changes over time are apparent; making a significant increase in pain immediately apparent.

Pain severity may be determined by one or more of: a number of action units present indicative pain; an amount of facial distortion corresponding to the change represented by the particular action unit concerned; or a degree of distortion determined with reference to reference information for that patient or for other patients.

The use of such indicators may allow embodiments to distinguish between levels of severity of pain, thereby providing a physician with additional information with which to treat the patient. For example, the level of severity may be used to determine the drug or dosage with which to treat the patient.

The feature or set of features may be facial features of the patient chosen from the list of:
 brow lowering;
 cheek raising;
 tightening of eyelids;
 wrinkling of nose;
 raising of upper lip;
 pulling at corner lip;
 horizontal mouth stretch;
 parting lips; and
 closing eyes.

The pain representation may comprise pain indicators corresponding to at least four of the facial features listed.

The method may comprise allocating a colour for the visual component of the pain indicator based on the determined severity of experienced pain. The human brain responds better to information portrayed in a graphical manner. Therefore, when the pain representation includes a number of pain indicators and each of the pain indicators is coloured according to a determined severity, the presentation of the pain indicators as a single pain representation may provide information relating to the pain experienced by the patient in a manner which is easier for a user to interpret. This may result in a quicker reaction and therefore more effective treatment.

One or more of the following may apply: no pain is associated with white, mild pain is associated with green, moderate pain is associated with yellow and severe pain is associated with red.

The method may further comprise continuously capturing the information indicative of changes to the features and updating the pain indicators and the pain representation to reflect changes over time to the features.

The predetermined time period may be 5 seconds and the pain indicators may be updated every 5 seconds. In an embodiment, the pain indicators for the last 80 seconds may be displayed.

The step of determining at least one pain indicator corresponding to each feature based on the captured information may be conducted automatically using an algorithm.

The method may further comprise determining a level of pain experienced by the patient based on the indicator.

The method according may further comprise providing an alarm if the determined level of pain exceeds a predetermined level.

The patient may be monitored by video and the information indicative of changes to the features may be image information.

The method may further comprise displaying a plurality of pain representations over a historical time period. The historical time period may be 80 seconds. Each of the pain representation may correspond to a selected time period. The selected time period may be 5 seconds.

A further embodiment extends to a pain assessment system comprising:
an interface for receiving information concerning at least two visible features or sets of features that are indicative of experienced pain over a predetermined time period;
a processor arranged to:
allocate at least one pain indicator corresponding to each feature or set of features based on the captured information, each pain indicator comprising a distinct visual component; and
collate all pain indicators to construct a pain level representation,
wherein the pain indicator is allocated in dependence on a determined pain severity, and
wherein the pain representation comprises a display of at least two pain indicators so that their corresponding visual components are simultaneously visible.

The visible facial features or set or features may correspond to facial expressions analysed using the FACS (Facial Action Coding System) methodology. The sets of features may correspond to action units. Each pain indicator may correspond to one or more action units.

The allocation of the pain indicator may be made with reference to reference information and the system may further comprise a data store for storing reference information concerning at least two visible features that are indicative of experienced pain In an embodiment, computer software has been pre-trained to determine which action units correspond to pain. In such an embodiment, the processor will refer to the reference information generated during training to determine whether or not a particular facial feature or set of facial features corresponds to pain. In addition, or alternatively, reference information pertaining to a patient who is experiencing no, or less, pain may be used and the allocation is then made on the basis of a determined increase in pain.

The feature or set of features may be facial features of the patient chosen from the list of:
brow lowering;
cheek raising;
tightening of eyelids;
wrinkling of nose;
raising of upper lip;
pulling at corner lip;
horizontal mouth stretch;
parting lips; and
closing eyes.

The pain representation may comprise pain indicators corresponding to at least four of the facial features listed.

The processor may be arranged to allocate a colour for the visual component of the pain indicator based on the determined severity of experienced pain.

The processor may be arranged to apply one or more of the following: no pain is associated with white, mild pain is associated with green, moderate pain is associated with yellow and severe pain is associated with red.

The processor may be arranged to continuously capture the information indicative of changes to the features and update the pain indicators and the pain representation to reflect changes over time to the features.

The processor may be arranged to further determine a level of pain experienced by the patient based on the representation.

The processor may be arranged to display a plurality of pain representations over a historical time period, each of the pain representations corresponding to a selected time period.

The system may further comprise an alarm.

The interface may be a video interface.

A further application extends to a software application installable on a user computing device, the application when installed on the user computing device causing the user computing device to operate in accordance with a pain assessment system arranged to:
receive information indicative of at least two features of a patient from a capturing element of the user computing device, the at least two features being indicative of experienced pain;
transmit the received information to a pain assessment system via a communications network such that the pain assessment system can determine a severity of experienced pain by allocating at least one pain indicator corresponding to each feature based on the captured information and collate each indicator to construct a pain representation; and
receive the pain representation from the pain assessment system via the communications network.

An aspect of the disclosure extends to a method for determining representation of pain experienced by a patient, the method comprising:
providing reference information concerning at least two visible features that are indicative of experienced pain;
capturing information indicative of changes to the features over time by observing the patient directly or indirectly over a predetermined time period;
allocating at least one pain indicator to each feature based on the captured information, each pain indicator comprising a distinct visual component; and
collating all pain indicators to construct the pain representation,
wherein the pain indicator is allocated in dependence on the determined severity, and
wherein the pain representation comprises a display of at least two pain indicators so that their corresponding visual components are simultaneously visible.

An aspect of the disclosure extends to a pain assessment system comprising:
a data store for storing reference information concerning at least two visible features that are indicative of experienced pain;
an interface for receiving information indicative of changes to the features over a predetermined time period;
a processor arranged to:
allocate at least one pain indicator corresponding to each feature based on the captured information, each pain indicator comprising a distinct visual component; and collate all pain indicators to construct a pain level representation,
wherein the pain indicator is allocated in dependence on the determined severity, and
wherein the pain representation comprises a display of at least two pain indicators so that their corresponding visual components are simultaneously visible.

An aspect of the disclosure extends to a software application installable on a user computing device, the application when installed on the user computing device causing the user computing device to operate in accordance with a pain assessment system arranged to:

receive information indicative of at least two features of a patient from a capturing element of the user computing device, the at least two features being indicative of experienced pain;

transmit the received information to a pain assessment system via a communications network such that the pain assessment system can determine a severity of experienced pain by allocating at least one pain indicator corresponding to each feature based on the captured information and collate each indicator to construct a pain representation; and receive the pain representation from the pain assessment system via the communications network.

An aspect of the disclosure extends to a method for determining a representation for a level of pain experienced by a patient, the method comprising: providing reference information concerning at least two visible features that are indicative of experienced pain; capturing information indicative of facial features by observing the patient directly or indirectly over a predetermined time period; allocating at least one pain indicator corresponding to each feature based on the captured information; and collating each indicator to construct the pain level indicator.

Embodiments will be more fully understood from the following description, with reference to the accompanying drawings.

DETAILED DESCRIPTION

Embodiments relate to a method and systems for determining for determining a representation of the amount of pain experienced by a patient. In this regard, information indicative of at least two visible features of a patient is captured that is capable of indicating pain experienced by the patient. The features may for example be facial features of the patient. Accordingly, the information may be in the form of an image of the face of the patient.

Using the captured information, quantitative pain indicating information is determined indicative of a level of pain experienced by the patient after a time period. By recognising facial features such as action units which are indicative of pain, the presence and severity of pain experienced by a patient may be determined. In this way, the level of pain experienced by a patient can be objectively assessed which is particularly advantageous for patients that are incapable of communicating the severity of pain that they experience, such as dementia patients or infants.

Furthermore, the method and system in accordance with embodiments have a real time, or near real time, functionality and capability which is particularly advantageous for its applicability for point-of-care use.

Suitable exemplary applications of the method and the system for determining a representation for a level of pain experienced by a patient may be used in the field of, but not limited to, dementia, autism and paediatrics. For example, the pain assessment system in accordance with embodiments may be used for dementia patients, autistic patients or infants and/or other population groups with difficulties in communicating pain. However, it will be appreciated that embodiments of the invention may be used in any suitable field in which a patient requires long term observation and is not limited to those patients who may have difficulties communicating.

Figure 1:
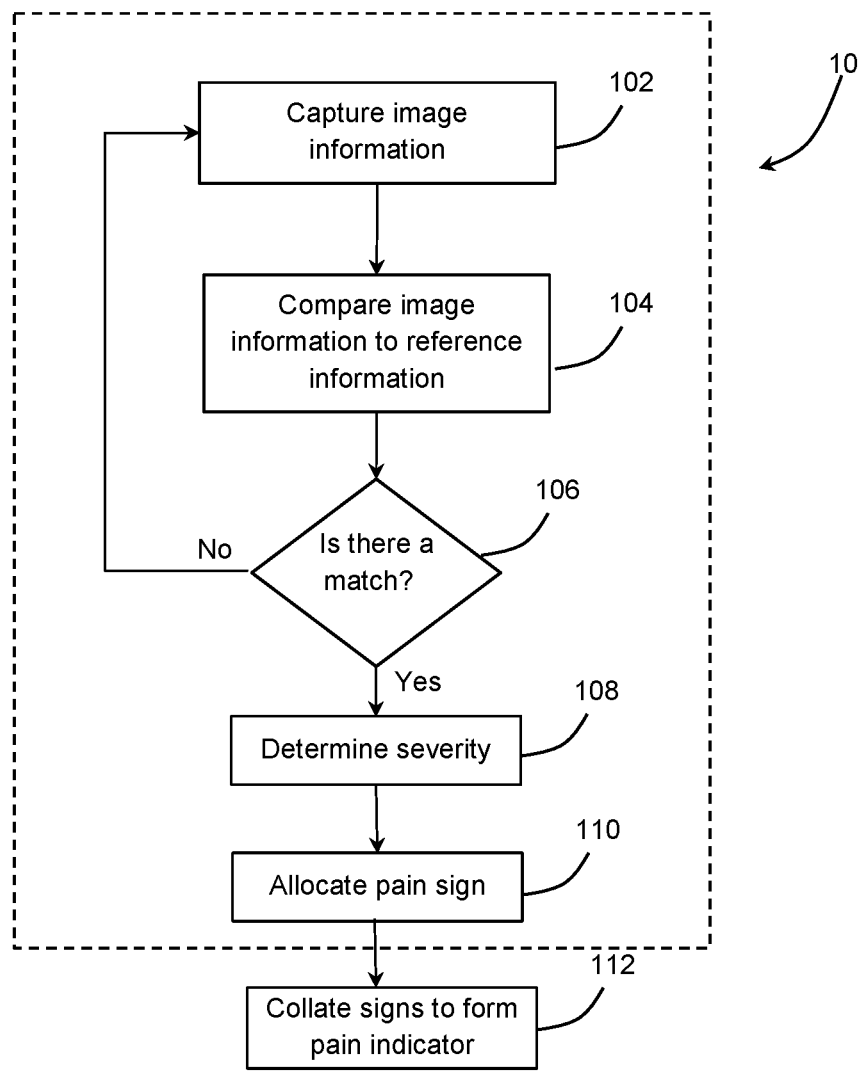
FIG. 1 is a flow chart of a method in accordance with an embodiment of the present invention.

Referring now to FIG. 1, there is shown a flow chart of a method for determining an indicator for a level of pain experienced by a patient. In a first step 102, first information is captured indicative of at least two visible features of a patient that are capable of indicating pain experienced by the patient.

In this embodiment, the system captures information relating to all of the following facial features: brow lowering; cheek raising; tightening of eyelids; wrinkling of nose; raising of upper lip; pulling at corner lip; horizontal mouth stretch; parting lips; and closing eyes. Each of these features correspond to an action unit as defined by the FACS (Facial Action Coding System) methodology. In this embodiment, the system will capture a set of frames (about 5 seconds worth) and the system has been trained to recognise action units in that information.

In the specific example shown in FIG. 1, a camera will monitor each of the features and capture image information at step 102. In FIG. 1, the steps 102 to 110 (as indicated by the dashed-line box) will be repeated for each of the facial features being monitored.

In a further step 104, the captured first information from step 102 is compared to reference information.

In this embodiment, the reference information is the information which the computer system has built up during the training phase and this is the information that the system uses to determine whether a corresponding action unit exists in the information captured.

For example, the software program may explore a method of identifying key muscles of the face of a patient and then linking points of the identified key muscles to create a map of the face of a patient. In this way, facial expressions may be analysed using the FACS (Facial Action Coding System) methodology. FACS is an anatomically based system and describes facial codings (or "action units") through specific muscle movement. Specifically, FACS divides facial muscles into action units that typically comprise a plurality of muscles. The plurality of muscles within an action unit is associated with predefined actions such as raising the inner left eyebrow or raising the left outer lip. Activation of a number of action units may be indicative of a facial expression, such as the expression of happiness or pain.

The software program may further be arranged to link the aforementioned measurements of the identified facial key muscles with human expressions such as presence or absence of pain. In this regard, the exemplary software program may use a database of images with facial expression in natural environments to learn from real examples.

In an alternate embodiment, during a calibration phase, the facial features of the patient are monitored to evaluate those features while the patient is not experiencing pain. In an alternate embodiment, the reference information comprises information relating to other patients for whom it may be easier to determine whether or not they are experiencing pain.

This step 104 is, in this embodiment, conducted automatically using an algorithm. The algorithm identifies the action units from the images of the patient captured by the camera.

At the following step, step 106, a determination is made as to whether there are one or more action units which are representative of experienced pain. In this embodiment, if action units corresponding to one or more action units corresponding to the following facial features are present, then the system will determine that there is a match at step 106: brow lowering; cheek raising; tightening of eyelids; wrinkling of nose; raising of upper lip; pulling at corner lip; horizontal mouth stretch; parting lips; and closing eyes.

If there is no such match, the process returns to step 102. However, if at least one action unit indicative of pain is detected, then the process proceeds to step 108 where a determination of the severity of the experienced pain, based on the features of the corresponding action unit, is made.

Generally each action unit will correspond to a particular facial distortion. The severity will then be determined with reference to a degree of that distortion. This may be done by comparison with information gleaned through a training process or by direct comparison with reference information for that patient, or for other patients.

Once a determination of severity is made in step 108, the process then allocates an indicator to the particular feature being monitored, based on the determined severity.

For example, one of the facial features monitored is the brow of the patient. At step 102 image information of the patient is obtained and the brow identified. Further, positional information of the brow relative to the face of the patient is determined and compared to predetermined data that is indicative of widely accepted pain indicators such as AGS's pain indicators.

A lowering of the brow is indicative of experienced pain. Therefore, at step 106 a determination is made of the position of the brow of the patient relative to the face, and if it is determined that the brow is lower than expected, a determination that there is a change indicative of experienced pain is made.

Furthermore, it is accepted that the degree to which the brow is lowered is indicative of the severity of the pain. Therefore, at step 108, a determination of the amount by which the brow is lowered is made, and a severity is allocated based on this at step 110.

The severity is divided into four categories and a colour is allocated based on the severity. No pain is associated with white, mild pain is associated with green, moderate pain is associated with yellow and severe pain is associated with red. In this embodiment, the indicator is a displayed rectangle, as described in further detail below with reference to FIG. 4.

A further facial feature may relate to the eyes of the patient. For this facial feature, a pain indicator may for example be tightening the eyelids or closing the eye. By determining positional information of the eye and the eye lids, it can be determined whether this facial feature conforms to one of AGS's pain indicators and a predefined severity of pain may be allocated.

For the facial feature of the mouth information relating to facial distortion such as raising the upper lip, pulling at corner lip, horizontal mouth stretch and parting lips is collected. In this regard, positional information of the mouth of the patient may be determined, such as a size, a position of the mouth relative to the face, a position of the lips relative to each other or a position of corners of the mouth. In this way, it can be determined whether the mouth of the patient conforms to any one or more of the above mentioned pain indicators.

In an alternate embodiment, a predefined score of pain may be allocated to each of the identified features. For example, a binary scoring system may be used in which presence of pain allocates a score of 1 whereas absence of pain is allocated a score of 0. Once scores of pain have been allocated to the identified facial features, a total level of pain for the plurality of facial features may be determined.

Figure 4:
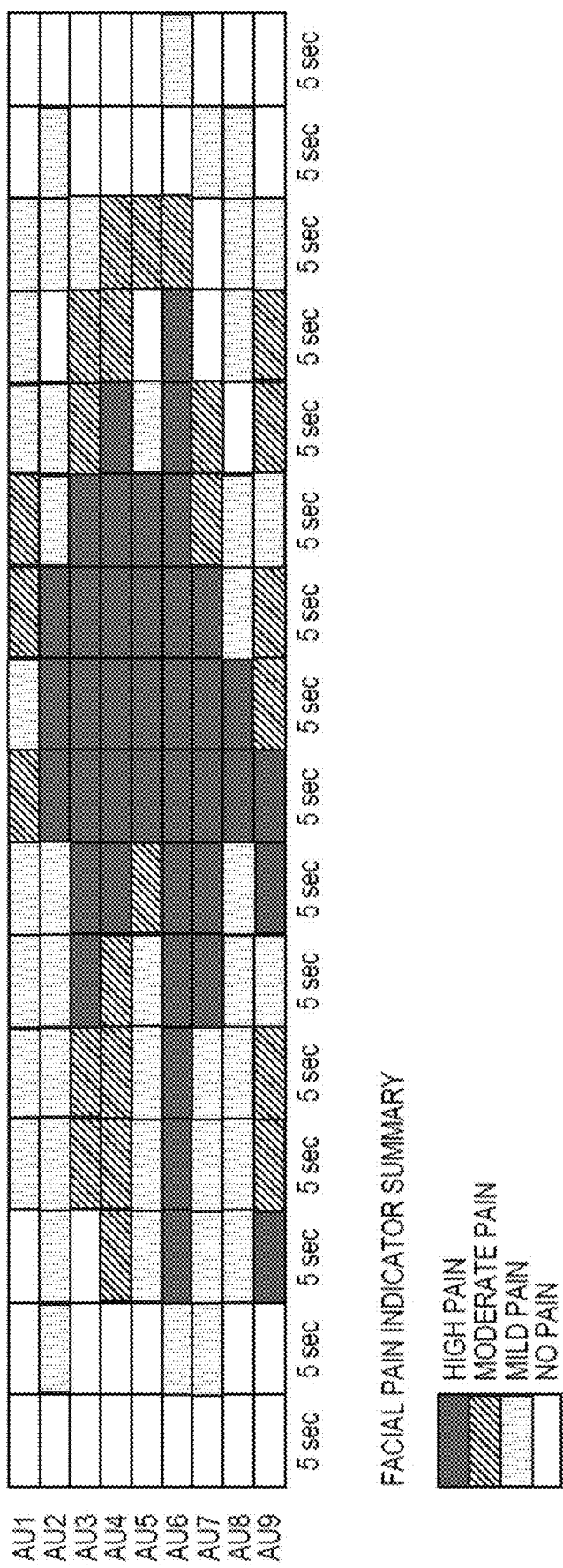
FIG. 4 illustrates a plurality of pain representations as generated by the system of FIGS. 2 and 3.

At step 112 each of the indicators allocated for each of the monitored facial features is collated into a pain representation. An example of such pain representations is illustrated in FIG. 4 where each of the rectangles corresponds to a pain indicator for a monitored facial feature. The representations are presented in the form of a table where each column represents a change monitored over a period of 5 seconds. Each row corresponds to a different facial feature. In this embodiment, the features are as follows:

| | |
|---|---|
| AU1 | Brow lowering |
| AU2 | Cheek raising |
| AU3 | Tightening of eyelids |
| AU4 | Wrinkling of nose |
| AU5 | Raising of upper lip |
| AU6 | Pulling at corner lip |
| AU7 | Horizontal mouth stretch |
| AU8 | Parting lips |
| AU9 | Closing eyes |

The severity is determined and the colour of the rectangle chosen as previously described. Therefore, each column is a pain representation since it may be representative of the pain experienced by the patient at that time.

This pain representation uses 5-second evaluation periods and displays the last 80 seconds worth of information gathered. It has been found that these values provide a useful representation to the user of the change in the experienced pain over time to the diagnostician or other medical personnel. Furthermore, this resolution provides a balance between keeping data visible for sufficient time for the human user to interpret it whilst keeping the refresh rate of the data short enough to capture fleeting changes in pain experience.

The colours of green, yellow and red have been chosen to represent little, moderate and serve pain, respectively. These are colours which users naturally associate with those levels of intensity. Therefore, these colours allow a user to quick assess the current and historical pain that the patient is experiencing.

In the embodiment shown all nine facial features are used. However, in further embodiments, a subset of facial features may be selected. This may be particularly useful where, for example, a patient has suffered a stroke or other malady affecting their facial expressions. This then ensures that only representative facial expressions are used. This could be tailored to the specific patient, using historical data, such as cultural data.

Advantageously, displaying the history of the determined pain indicators may provide a representation of the changes to the experienced pain, further assisting in the determination and treatment of the pain.

Furthermore, an alarm may be set for a combination of indicators and levels of severity. This may depend on the particular patient or other circumstances.

Figure 2:
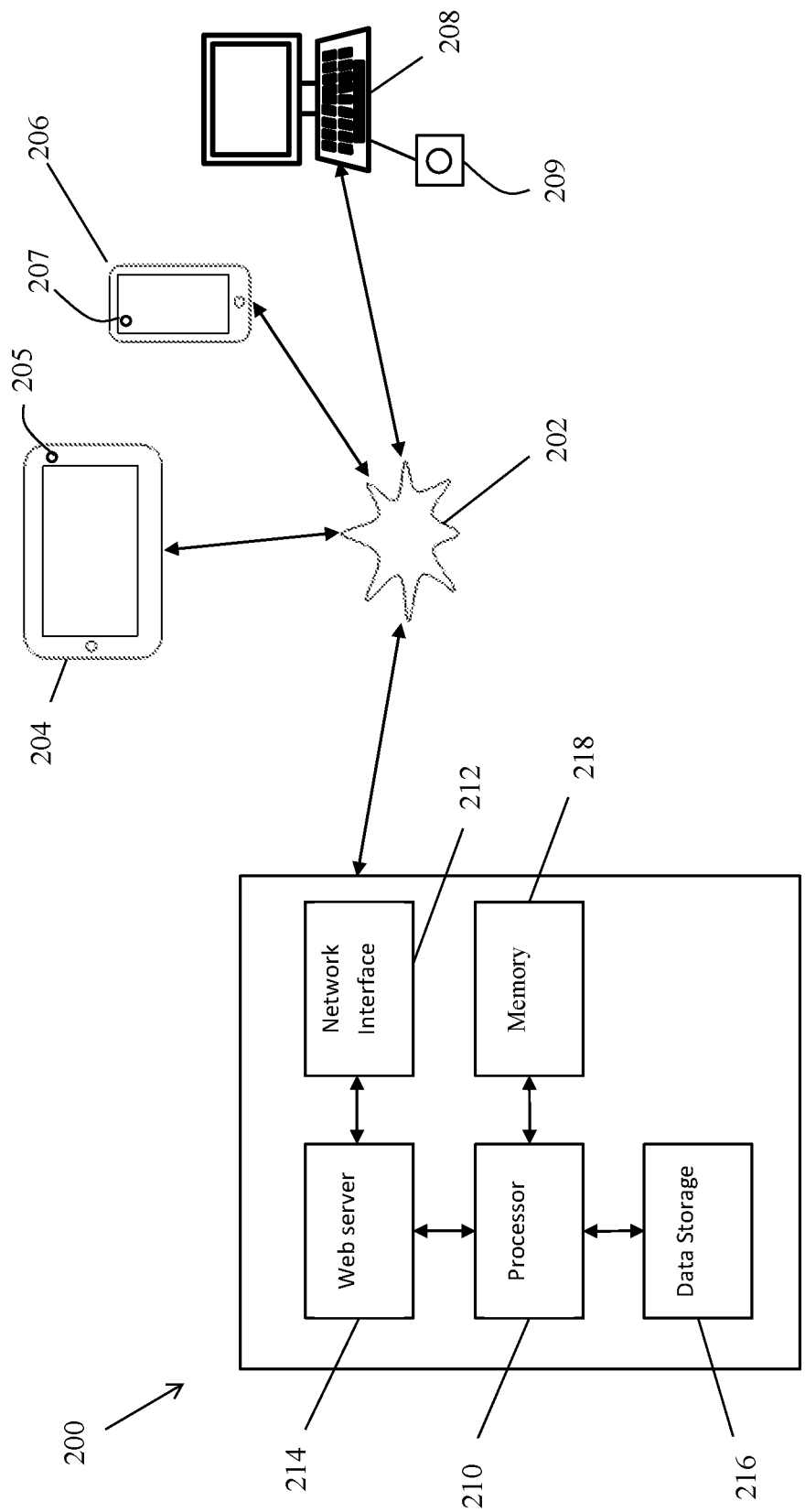
FIG. 2 is a schematic representation of a pain assessment system in accordance with an embodiment of the present invention.

Referring now to FIG. 2, there is shown a schematic representation of a system 200 for determining a representation for a level of pain experienced by a patient. In this example, the pain assessment system 200 is in the form of a computer server that is accessible through a communications network 202 from user computing devices 204, 206, 208, each provided with a corresponding camera 205, 207 and 209 which is used to collect image information of the face of a patient. The communications network 202 may be any suitable network such as the Internet, cloud computing or a peer-to-peer network such as Bluetooth. In this example, the user computing devices 204, 206, 208 include a tablet computer 204, a smartphone 206, and a personal computer 208. However, it will be understood that any communications enabled computing device that is capable of communicating with the pain assessment system 200 is envisaged, such as a laptop computer or PDA. Furthermore, the camera may be integrated into the device or be provided separately thereto.

In the present example, the pain assessment system 200 is implemented as a computer server including a processor 210 arranged to control and coordinate operations in the system 200. The system 200 further comprises a network interface 212 which in this example is arranged to facilitate wireless communications with the system 200 through the Internet 202. In the present embodiment as shown in FIG. 2, the system 200 is accessible by the user computing devices 204, 206, 208 through web pages served to the user computing devices 204, 206, 208 by a web server 214. In a specific example, this is realised by software implemented by the processor 210, and through an application programming interface (API) that communicates with the user computing devices 204, 206, 208 using a dedicated application installed on the user computing devices 204, 206, 208. However, other implementations are envisaged.

The system 200 also includes a data storage 216 arranged to store programs, data and information used by the system 200. The system 200 also includes a memory 218 used by the processor 210 to temporarily store data and programs used by the processor 210 to implement functionality in the system 200.

Figure 3:
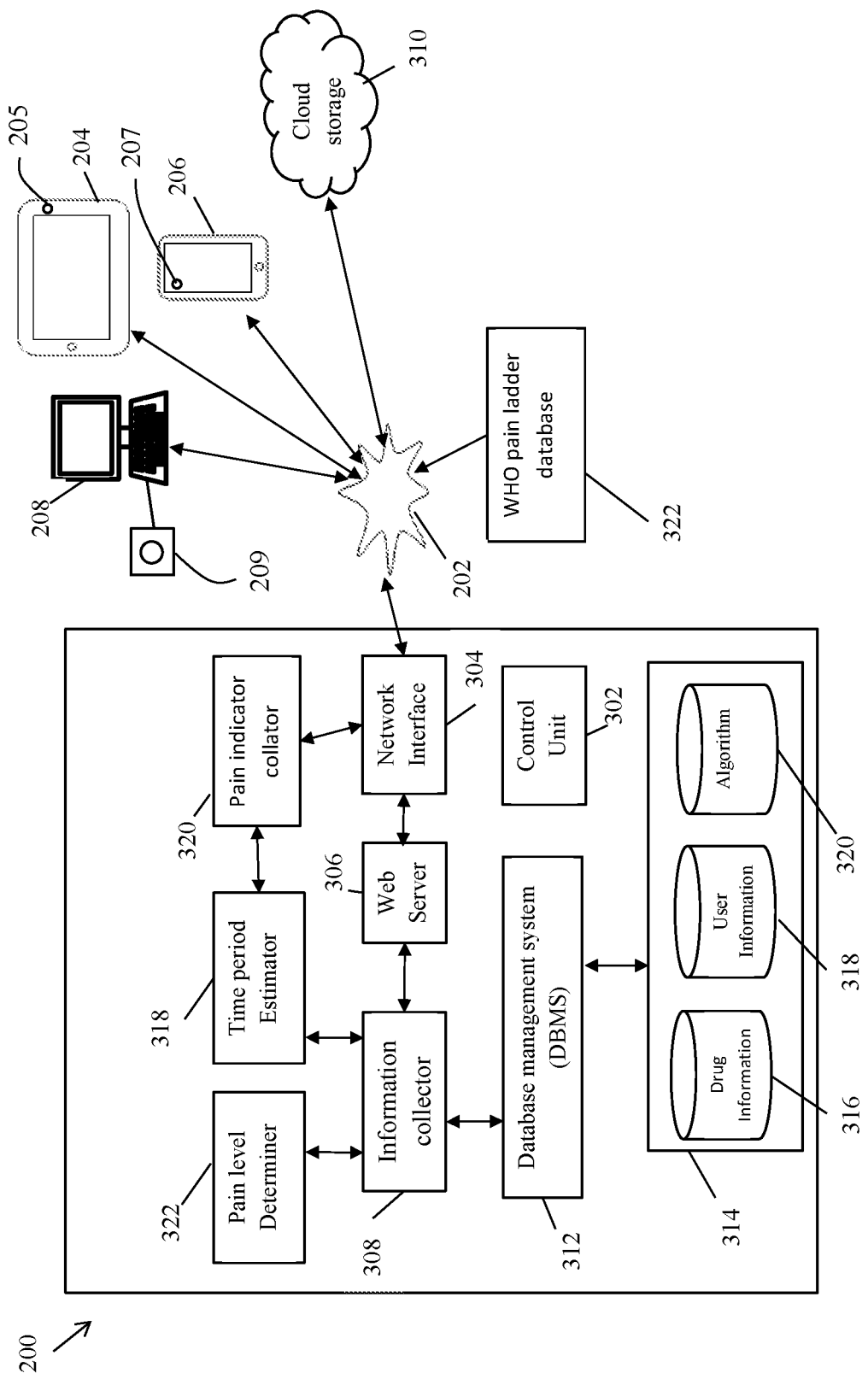
FIG. 3 is an alternative representation of the system of FIG. 2.

A representation of an example implementation of the pain assessment system 200 is shown in FIG. 3, with functional components of the system 200 shown instead of hardware components. It will be understood that the functional components in this example may be implemented using the hardware components shown in FIG. 2 such that network interfaces are provided for facilitating communications with remote user computing devices 204, 206, 208 and implementing actions in response to the communications.

The pain assessment system 200 in this example comprises a control unit 302 for controlling and coordinating operations of the components of the system 200. This control unit 302 may for example be implemented by the processor 210 shown in FIG. 2.

Further, the system 200 has a network interface 304 for facilitating communications through the communications network 202, such as the Internet between the system 200 and remote computing devices, such as user computing devices 204, 206, 208. In this example, a web server 306 of the system 200 is arranged to serve one or more webpages to the user computing device 204, 206, 208 that can be accessed through a browser installed on the user computing device 204, 206, 208 thereby facilitating communications with the system 200.

In this specific example as shown in FIG. 3, the system 200 is arranged to receive at an information collector 308 the image information collected by the cameras 205, 207 and 209. The captured image is then transmitted to the system 200 by uploading the captured image using a web page displayed on the user computing device 204, 206, 208 served by the web server 306 of the system 200. Alternatively, the image information may be received at the information collector 308 of the system 200 by importing data from a remote database such as a cloud storage 310.

The pain assessment system 200 further comprises a data base management system ("DBMS") 312 that is arranged to store the information that is received at the information collector 308 in a data storage 314 of the system 200. A person skilled in the art will appreciate that the information may alternatively be stored in a data storage system that is not part of the system 200. For example, the information may be stored in a cloud storage 310 and may be received at the system 200 through the Internet 202 via the network interface 304.

In response to receiving a first image of the facial feature of the patient at the information collector 308, a pain level determiner 322 of the pain assessment system 200 uses the first image to determine information indicative of a first level of pain experienced by the patient. In this particular example, the information represents reference information for a level of pain experienced by the patient before a drug is administered.

The pain level determiner 322 determines whether the facial feature is indicative of experienced pain and the severity of the pain, as described above automatically using an algorithm. The algorithm is stored by the DBMS 312 in an algorithm database 316 of the data storage 310. In this particular example, the algorithm that is used for determining the information indicative of a level of pain may identify a facial feature from the first image and compare this identified facial feature with a previously stored image or images and predetermined data such as AMS's widely accepted pain indicators. In this example, the predetermined data is also stored in the algorithm database 316. However, it will be envisaged that the predetermined data may be stored remote relative to the system 200, for example in the cloud storage 310.

The system 200 further comprises a pain representation collator 320 which collates the pain indicators allocated by the pain level determiner 322 into a pain representation as illustrated in FIG. 4. The pain representation collator 320 communicates with the network interface and the web server 306 to display the information to the user computing devices 204, 206, 206. This may be done by using dedicated application software that is installed on the user computing device 204, 206, 208 or in any other suitable manner.

The processor 210 of the system 200 may optionally be arranged to determine treatment of the patient based on the collated pain representation. For example, if the level of experienced pain is above a predetermined threshold then the administration of a specific analgesic at a specified dose may be recommended.

Although the system 200 of FIGS. 2 and 3 provides a server client model, it is also possible to implement an embodiment as a standalone device which does not rely on Internet or other communications connections. This may be particularly advantageous in remote communities without communications infrastructure.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

What is claimed is:

1. A method for determining a representation of pain experienced by a patient, the method comprising:
    capturing information concerning at least two visible features or sets of features that are indicative of experienced pain by observing a patient directly or indirectly over a predetermined time period;
    allocating at least one pain indicator to each feature or set of features based on the captured information, each pain indicator comprising a distinct visual component; and
    collating all pain indicators to construct a pain representation,
    wherein the pain indicator is allocated in dependence on a determined pain severity,
    wherein the pain representation comprises a display of at least two pain indicators so that their corresponding visual components are simultaneously visible, and
    wherein each pain indicator corresponds to a different feature or set of features, and the at least two pain indicators correspond to at least four facial features.

2. The method according to claim 1 wherein the facial features are chosen from the list of:
    brow lowering;
    cheek raising;
    tightening of eyelids;
    wrinkling of nose;
    raising of upper lip;
    pulling at corner lip;
    horizontal mouth stretch;
    parting lips; and
    closing eyes.

3. The method according to claim 1, comprising allocating a colour for the visual component of the pain indicator based on the determined severity of experienced pain.

4. The method according to claim 3 wherein one or more of the following apply: no pain is associated with white, mild pain is associated with green, moderate pain is associated with yellow and severe pain is associated with red.

5. The method according to claim 1, further comprising continuously capturing the information indicative of changes to the features and updating the pain indicators and the pain representation to reflect changes over time to the features.

6. The method according to claim 1, wherein the step of determining at least one pain indicator corresponding to each feature based on the captured information is conducted automatically using an algorithm.

7. The method according to claim 1, further comprising determining a level of pain experienced by the patient based on the representation.

8. The method according to claim 7 further comprising providing an alarm if the determined level of pain exceeds a predetermined level.

9. The method according to claim 1, wherein the patient is monitored by video and wherein the information indicative of changes to the features is image information.

10. The method according to claim 1, further comprising displaying a plurality of pain representations over a historical time period, each of the pain representations corresponding to a selected time period.

11. A pain assessment system, comprising:
    an interface for receiving information concerning at least two visible features or sets of features that are indicative of pain experienced by a patient over a predetermined time period;
    a processor arranged to:
        allocate at least one pain indicator corresponding to each feature based on the information captured via the interface, each pain indicator comprising a distinct visual component; and
        collate all pain indicators to construct a pain representation,
        wherein the pain indicator is allocated in dependence on a determined pain severity,
        wherein the pain representation comprises a display of at least two pain indicators so that their corresponding visual components are simultaneously visible, and
        wherein each pain indicator corresponds to a different feature or set of features, and the two pain indicators correspond to at least four facial features.

12. The system according to claim 11, wherein the facial features are facial features of the patient chosen from the list of:
    brow lowering;
    cheek raising;
    tightening of eyelids;
    wrinkling of nose;
    raising of upper lip;
    pulling at corner lip;
    horizontal mouth stretch;
    parting lips; and
    closing eyes.

13. The system according to claim 11, wherein the processor is arranged to allocate a colour for the pain indicator based on the determined severity of experienced pain.

14. The system according to claim 13, wherein the processor is arranged to apply one or more of the following: no pain is associated with white, mild pain is associated with green, moderate pain is associated with yellow and severe pain is associated with red.

15. The system according claim 11, wherein the processor is arranged to continuously capture the information indicative of changes to the features and update the pain indicators and the pain representation to reflect changes over time to the features.

16. The system according to claim 11, wherein the processor is arranged to further determine a level of pain experienced by the patient based on the representation.

17. The system according to claim 16, further comprising an alarm.

18. The system according to claim 11, wherein the interface is a video interface.

19. The system according to claim 11, wherein the processor is arranged to display a plurality of pain representations over a historical time period, each of the pain representations corresponding to a selected time period.

* * * * *